United States Patent [19]

Sako et al.

[11] 3,940,802

[45] Mar. 2, 1976

[54] MEDICAL APPLIANCE MADE OF PLASTIC

[75] Inventors: Eiji Sako, Osaka; Hisasi Sasamoto, Matsubara, both of Japan

[73] Assignee: The Green Cross Corporation, Japan

[22] Filed: Jan. 24, 1975

[21] Appl. No.: 544,008

[52] U.S. Cl. .................................. 3/1.4; 3/1; 3/1.5; 128/214 D; 128/272; 260/32.4; 260/873

[51] Int. Cl.² .... A61F 1/24; A61F 1/22; A61F 1/00; A61M 5/14

[58] Field of Search .......................... 3/1, 1.4–1.7; 128/214 R, 214 C, 214 D, 272, DIG. 24; 260/873, 32.4 R

[56] References Cited
UNITED STATES PATENTS

| | | | |
|---|---|---|---|
| 2,896,619 | 7/1959 | Bellamy | 128/214 D |
| 3,511,684 | 5/1970 | Huffaker | 3/1 X |
| 3,562,352 | 2/1971 | Nyilas | 3/1 X |
| 3,574,789 | 4/1971 | Bungs et al. | 260/873 |
| 3,609,768 | 10/1971 | Ayres | 3/1 |
| 3,717,502 | 2/1973 | Masuhara et al. | 3/1 X |

OTHER PUBLICATIONS

Concise Guide to Biomedical Polymers, Their Design, Fabrication and Molding, by John W. Boretos, Charles C. Thomas (Publisher), pp. 30–31.

*Primary Examiner*—Ronald L. Frinks
*Attorney, Agent, or Firm*—Cushman, Darby & Cushman

[57] ABSTRACT

A medical appliance suitable for use in direct or indirect contact with blood, such as an artificial valve, artificial blood vessel, blood transfusion set, solution infusion set, or blood bag characterized by being composed of 100 parts by weight of polyvinyl chloride and as plasticizer 50 to 100 parts by weight of thermoplastic polyurethane of the polyester type, said polyurethane having a softening point of about 70°C and giving no spot other than that of the origin at the same position loaded the test sample onto the plate in thin-layer chromatogram.

6 Claims, No Drawings

MEDICAL APPLIANCE MADE OF PLASTIC

This invention relates to a medical appliance made of polyvinyl chloride and, more particularly, to a medical appliance made of polyvinyl chloride suitable for use in direct or indirect contact with human blood, such as an artificial valve, artificial blood vessel, blood transfusion set, solution infusion set, or blood bag.

Many of the above-noted medical appliances have heretofore been made of plastic materials which meet the non-toxicity requirements specified in the Japanese Pharmacopeia when tested according to the specified testing methods such as, for example, the testing method for plastic containers used in medical solution for infusion (solution infusion). In such plastic materials, polyvinyl chloride is widely used because it is inexpensive, is available in a broad range of stiffness from flexible to rigid depending on the plasticizer content to serve for various purposes, and, moreover, is transparent and easy-processing.

Quite recently, however, it has been suggested that serious diseases might be caused if the human body takes in, through the blood contacted with a polyvinyl chloride plastics, phthalate esters including dioctyl phthalate which had long been believed to be a non-toxic plasticizer [for example J. Neergaard et al., Scand. J. Urol., Nephrol., 5, 141 (1971); R. J. Jaeger et al., New Eng. J. Med., 287 (22), 1,114 (1972); T. J. Contreras et al., Transfusion, 14, (1), 34 (1974); and Medical Stoff Conference, California Medicine, 112 (2), 43 (1970)].

When a fabricated article of polyvinyl chloride plasticized with a phthalate ester is brought into contact with blood, some amount of the phthalate ester migrates into the blood. It is known, for instance, that from a blood bag made of polyvinyl chloride, a phthalate ester migrates into the stored blood in the bag and is accumulated in human tissues after transfusion of stored blood (R. J. Jaeger et al., loc. cit.). The present inventors also made it clear by a test that various plasticizers are extractable with blood plasma from plasticized polyvinyl chloride even if the plasticizer content is very low.

The object of this invention is to provide medical appliances made of plasticized polyvinyl chloride which contain no such toxic substances as are extractable with blood.

According to this invention, there is provided a medical appliance suitable for use in direct or indirect contact with human blood, characterized by being fabricated from plasticized polyvinyl chloride comprising 100 parts by weight of polyvinyl chloride and 50 to 100 parts by weight of thermoplastic polyester-based polyurethane used as plasticizer, said polyurethane having a softening point of about 70°C and giving in a thin-layer chromatogram no spot other than the one at the original position where the test sample has been loaded onto the silica gel plate.

The thermoplastic polyurethane of the polyester type has a straight chain structure and composed of a polyester component and an alkylene or polyoxyalkylene diisocyanate component. The polyester component is derived from an aliphatic diol having at least 6 carbon atoms and an aliphatic dicarboxylic acid having at least 6 carbon atoms and its hydroxyl value of the polyester being 50 to 60. The softening point of the polyurethane is about 70°C. Such a polyester-based polyurethane, contrary to the polyester-based type, is found to be sufficiently compatible with polyvinyl chloride to form plasticized polyvinyl chloride. The amount of thermoplastic polyester-based polyurethane to be incorporated in polyvinyl chloride ranges from 50 to 100 parts by weight for 100 parts by weight of the latter corresponding to a wide range of stiffness, from flexible to nearly rigid, necessary for the fabricated articles to serve for various uses. The amount to be incorporated, for example, is 60 to 90 parts by weight for a blood bag or an infusion set, 50 to 70 parts by weight for an artificial valve, and 70 to 100 parts by weight for an artificial blood vessel.

The polyurethane to be used should not contain any of the impurities which, on being tested by thin-layer chromatography, give spots other than the one at the original position where the test sample has been loaded. If plasticized with a polyurethane containing such an impurity, the resulting polyvinyl chloride material does not meet the requirements specified in the Japanese Pharmacopeia and contains an impurity which tends to migrate into blood plasma and is easily identifiable by means of gas chromatography.

The thin-layer chromatography for selecting a proper polyurethane is carried out in accordance with the procedure described by Y. L. Marcel et al. [Lancet, 1, 35 (1970)]. Five grams of shaped polyurethane strips, 1.5 cm in length, 0.5 cm in width, and 0.4 to 0.5 mm in thickness, was placed in a flask, to which is then added 100 ml of chloroform. The flask is closed tightly with a stopper and kept at room temperature for 3 hours. The contents of the flask are filtered and the filtrate is evaporated to dryness at a temperature below 50°C under reduced pressure. To the residue is added 10 ml of methanol to obtain a sample solution. A 10-$\mu$l portion of the sample solution was spotted on a silica gel layer, 0.25 mm in thickness, to carry out thin-layer chromatography [solvent: n-hexane-ethyl acetate (9 : 1); temperature: room temperature; developed distance: 10 cm]. The spot developed on the thin-layer is detected by exposing to iodine vapor.

The gas chromatography for identifying an impurity migrated into blood plasma is carried out in the following way. Two grams of sample strips of the same size as used above is extracted three times with each 10 ml of blood plasma. The combined extract solution is extracted three times with a chloroform-methanol (2 : 1 volume) mixture and the combined extract solution is evaporated to dryness. The residue is dissolved in 1 ml of methanol to obtain a sample solution. The sample solution is subjected to programmed-temperature gas chromatography by use of ChromoSorb G-NAW, (NIHON CHROMATO WORKS, LTD.-JOHNS-MANNVILLE, U.S.A., purified siliceous earth, Kieselguhr.) as support. Any impurity, if present, can be detected from the peak in gas chromatogram.

If polyurethane, especially in case of the appliance to a bag, is incorporated in excess of 100 parts by weight for 100 parts by weight of polyvinyl chloride, the water vapour permeability through the wall of the plasticized polyvinyl chloride bag increases undesirably, while if the incorporated amount of polyurethane is below 50 parts by weight, the plasticizing effect is unsatisfactory. The plasticized polyvinyl chloride can be further incorporated with a stabilizer such as stearate.

The medical appliance of this invention can be manufactured by hot-milling the compounded polyvinyl chloride, pelletizing the milled polyvinyl chloride, and then shaping the pellets by customary processing procedures such as extrusion, calendering, etc. The fabricated articles are transparent, withstand sterilization by ethylene oxide gas or high-pressure steam (autoclaving), and have acceptable quality, as tested by extraction with blood plasma. The evaporation loss of aqueous solution through the wall of a bag does not exceed 4.0%, a limit specified in Notification of Ministry of Health and Welfare (Japan).

The invention is illustrated below in more detail with reference to Example, however the invention is not limited to the Example.

Example and Comparative Example
Polyvinyl chloride (PVC):
  Mean polymerization degree, 1,100;
  Manufactured by suspension polymerization;
  Amount used, 100 parts by weight.
Polyurethane:
  A: does not give any spot due to impurities on thin-layer chromatogram; softening point, about 70°C.
  B: gives a number of spots ($R_f$ = 0.17, 0.22, 0.55, 0.62, and 0.90) on thin-layer chromatogram; softening point, about 70°C.
  Amount incorporated: as shown in Table 1.
Stabilizer:
  Zinc stearate: 1.5 parts by weight.
  Calcium stearate: 0.7 part by weight.
Pelletization:
  Sheeting formed by means of a pair of milling rolls at 150° to 160°C from compounded polyvinyl chloride was cut into pellets.
Shaping:
  Tubing extruded from an extruder (L/D of screw = 26/1; compression ratio, 3.5) at 140° to 190°C. was heat-sealed to form a bag, 0.45 mm in wall thickness.
Test results: as shown in Table 1.

1. The containers do not interact physically or chemically with the contained medicament in any manner to alter the property or quality, and do not permit the invasion of microorganisms.

2. Transparency and appearance: The containers have a transparency which does not practically interfere with the test for foreign matter specified in General Rules for Preparations, Injections (10). The containers do not have stripes, cracks, bubbles, or other faults which make it difficult to be used.

3. Permeability: Fill the container with water equivalent to the labeled volume. After closing it hermetically, weigh accurately, and allow to stand for 14 days at a humidity of 65 ± 2%, and at a temperature of 20 ± 2°, then weigh accurately. The loss in weight is not more than 0.20%.

4. Heavy metals: Place 1.0 g of cut pieces of the container into a porcelain crucible and perform the test, according to Method 2 of Heavy Metals Limit Test. Prepare the control solution with 2.0 ml of Standard Lead Solution.

5. Residue on ignition: Weigh accurately about 5 g of cut pieces of the container, and perform the test according to the Residue on Ignition; the residue is not more than 0.10%.

6. Extractive substances: Take the container at the homogeneous parts of less bend and possibly same thickness, cut it into a piece having about 1,200 cm² of total surface area when the thickness is 0.5 mm or less, or about 600 cm² when the thickness is greater than 0.5 mm; subdivide into strips approximately 0.5 cm in width and 5 cm in length. Wash them with distilled water for injection, and dry at room temperature. Place these strips into 300 ml glass container complying with Glass Containers for Injections, (4) Soluble alkali test, add 200 ml of distilled water for injection, and fuse or Table 1

| | Polyurethane | | | |
| --- | --- | --- | --- | --- |
| | Type | Amount in parts by weight per 100 parts by weight of PVC | Peak in gas chromatogram due to impurity in plasma extract | Result of tests specified in Japanese Pharmacopeia | Evaporation loss of aqueous solution in % (20±2 °C, RH 65±2 %, 14 days) |
| Example | A | 50<br>80<br>100 | none<br>none<br>none | Acceptable | 0.89<br>2.54<br>3.07 |
| Comparative Example | B | 100 | A number of peaks due to impurities | 1. Water extraction test: unacceptable with respect to pH, reducing substance, UV absorption spectrum.<br>2. Hemolysis test: unacceptable.<br>3. Implantation test: unacceptable. | |

For reference, testing methods specified in Japanese Pharmacopeia are reproduced herein.

Plastic Containers for Aqueous Infusions:

The plastic containers for aqueous infusions should have a capacity of 500 ml or more, and be used as containers for aqueous infusions. They meet the following requirements. When the surfaces of them are coated, the material before coating must be used for the tests (4)-(11).

close tightly with a suitable stopper. With high pressure steam sterilizer, heat it at 121° for 1 hour, and allow to stand until the temperature lowers to room temperature, and use this solution as the test solution. Prepare the blank solution with distilled water for injection in the same manner. Perform the following tests with the test solution and the blank solution.

i. Description: The test solution is colorless and clear.

ii. foam test: Place 5 ml of the test solution in a glass-stoppered test tube of about 15 mm in innner diameter, and shake vigorously for 3 minutes. The formed foams disappear almost within 2 minutes.

iii. pH: To each 20 ml of the test solution and the blank solution, add 1.0 ml of potassium chloride solution containing 0.1 w/v% of potassium chloride in distilled water for injection. The difference of pH between them should not be more than 1.5 when measured by pH meter.

iv. Chloride: Place 10 ml of the test solution in a Nessler's tube, perform the test according to Chloride Limit Test. Prepare the control solution with 0.7 ml of 0.001 N hydrochloric acid.

v. Sulfate: Place 20 ml of the test solution in a Nessler's tube, perform the test according to Sulfate Limit Test. Prepare the control solution with 2.0 ml of 0.001 N sulfuric acid.

vi. Phosphate: Place 50 ml of the test solution in a Nessler's tube, add 2.5 ml of ammonium molybdatesulfuric acid TS and 1.0 ml of 1-amino-2-naphthol-4-sulfonic acid TS, shake well, and allow to stand for 20 minutes. The solution has no more color than the following control solution.

Control solution: Instead of the test solution, use 50 ml water solution containing 0.30 ml of Standard Phosphoric Acid Solution, and proceed in the same manner.

vii. Ammonium: Place 10 ml of the test solution in a Nessler's tube, add sufficient water to make 50 ml, add 2.0 ml of sodium hydroxide solution (1 → 3) and 1.0 ml of Nessler's TS, and shake well. The solution has no more color than the following control solution.

Control solution: Instead of the test solution, use 2.5 ml of Standard Ammonium Solution, and perform in the same manner.

viii. Heavy metals: Place 10 ml of the test solution in a separater, add 40 ml of water, 1.0 ml of ammonium citrate solution and 2 drops of methylred TS, and add strong ammonia water dropwise until the solution develops a yellow color, and then add 1.0 ml of strong ammonia water, 10 ml of dithizonebenzene solution, shake vigorously for 1 minute, and drain off the water layer. Then add 50 ml of diluted strong ammonia solution (1 → 100), shake vigorously for 30 seconds, and allow to stand, separate the benzene layer. Read the absorbance AT at the wavelength at 525 m$\mu$ in a 10 mm cell, using benzene as the blank. With 10 ml of Standard Lead Solution for Dithizone Method and with 10 ml of water, proceed in the same manner as the test solution, and determine the absorbances, As and Ao respectively; (At - Ao) does not exceed (As - Ao). Ammonium citrate solution and dithizone-benzene solution correspond to the test solutions for Lead Determination (Dithizone Method).

ix. Potassium permanganate-reducing substances: Place 20 ml of the test solution in a glass-stoppered Erlenmeyer flask, add 20 ml of 0.01 N potassium permanganate and 1.0 ml of dilute sulfuric acid, and boil for 3 minutes. After cooling add 0.10 g of potassium iodide and 5 drops of starch TS, titrate with 0.01 N sodium thiosulfate. Use 20 ml of water instead of the test solution, and perform in the same manner. The difference of the volume of consumed 0.01 N potassium permanganate is not more than 1.0 ml.

x. Residue on Evaporation: Measure 20 ml of the test solution, evaporate to dryness on a water bath, and dry the residue at 105° for 1 hour. The weight of residue is not more than 1.0 mg.

xi. UV Spectrum: Read the absorbance of the test solution at the maximum wavelength at 220 m$\mu$ in a 10 mm cell, using water as the blank: it exhibits no more than 0.30.

7. Acute systemic toxicity: The material meets the requirements, when the test solutions A and B are examined under following conditions against the blank solutions A' and B'.

Preparation of the test solution A and the blank solution A': From a homogenous and preferably flat part of plastic sample take by cutting a portion having the area equivalent to about 1800 cm$^2$ when the thickness is 0.5 mm or less, or 900 cm$^2$ when the thickness is greater than 0.5 mm; subdivide the sample into strips about 5 cm in length and about 0.5 cm in width. Wash and rinse the strips with neutral detergent solution, water and Distilled Water for Injection successively, and dry under clean condition at room temperature. Transfer the strips to a 500 ml flask which meets the requirements of (4) Soluble alkali test in Glass Containers for Injections, and add 300 ml of physiological saline. Seal the opening by fusing or with a suitable cap. Heat in an autoclave at 121° for 1 hour, and cool by allowing to stand to room temperature. The solution thus obtained is used as the test solution A. The blank solution A' is prepared in the same manner.

Preparation of the test solution B and the blank solution B': Prepare the strips of plastic material, wash and rinse, and dry, according to the procedure under preparation of the test solution A and the blank solution A', transfer to about 500 ml glass flask and add 300 ml of ethanol-physiological saline. Seal the opening by fusing or with a suitable cap and extract by heat at 70° for 24 hours, and cool to room temperature. The solution thus obtained is used as the test solution B. The blank solution B' is prepared in the same manner.

i. Test procedures

Test animals: Use healthy male mice of imbred strain or closed colony weighing 17 – 23 g.

Procedure: Inject intravenously to groups of 10 mice 50 ml per kg of each solution of the test and blank.

ii. Interpretation

Observe the animals for 5 days after injection. During the observation period, all animals treated with the extracts of the sample show no death as in the animals treated with the blank.

8. Intracutaneous reactivity test: The material meets the requirements, when the test solutions A and B specified in (7) are examined under following conditions against the blank solution A' and B'.

i. Test procedure

Test animal: Use healthy male rabbits weighing not less than 2.5 kg.

Procedure: Use groups of 2 rabbits for each sample. To a group, inject 0.2 ml of extracts intracutaneously to 10 sites of one side of the animals back for the test solution A and 5 sites of opposite side for the blank solution A'. For another group, the test solution B and the blank solution B' are examined in the same manner.

ii. Interpretation

Observe the injection sites at 24, 48 and 72 hours after injection. At the observation times, any tissue reaction such as erythema, edema, bleeding and necrosis is absent as in the animals treated with the blank.

9. Pyrogen Test: The test solution A specified in (7) meets the requirements of Pyrogen Test as well as the blank solution A'.

10. Hemolysis test: The sample meets the requirements of the test, when hemolysis is not observed after adding 0.1 ml of defibrinated blood of rabbit to 10 ml of the test solution A specified in (7) and allowing the mixture to stand at 37° for 24 hours. Using 10 ml of the blank solution A', perform the blank test in the same manner.

11. Implantation test: Prepare the 8 sample strips for implantation by cutting the plastics to the size of about 10 mm long and about 1 mm wide. Sterilize after rising with neutral detergent solution, water, and Distilled Water for Injection successively. Another 4 strips are prepared with negative control plastics for implantation test in the same manner.

The sample meets the requirements of the test when examined under the following conditions against control.

i. Test procedure

Test animal: Use two healthy male rabbits weighing not less than 2.5 kg.

Procedure: Insert each one test strip in a sterilized 15-gauge needles beforehand. Into the paravertebral muscles of one side of each of 2 rabbits, implant 4 strips of the sample with stylet, placing the strips at the sites about 2.5 cm apart from each other and about 3.5 cm from the spinal column. In the same manner, implant 2 strips of control in the opposite side of each animal.

ii. Interpetation

Keep the animals for a period of 72 hours after implantation, and sacrifice by anesthesia and then bleed. Examine the area of tissues surrounding the center portion of each implant strip macroscopically. Use magnifying glass if necessary. The tissues should free from changes such as hemorrhage or encapsulation as in the control, or the reaction should be observed at less than 1 of 4 sites in each animal.

What is claimed is:

1. A medical appliance suitable for use in direct or indirect contact with human blood, characterized by being fabricated from plasticized polyvinyl chloride comprising 100 parts by weight of polyvinyl chloride and 50 to 100 parts by weight of thermoplastic polyesterbased polyurethane used as plasticizer, said polyurethane having a softening point of about 70°C and giving in a thin-layer chromatogram no spot other than the one at the original position where a test sample has been loaded.

2. A blood bag according to claim 1, wherein the amounts of the thermoplastic polyester-based polyurethane are 60 to 90 parts by weight.

3. An infusion set according to claim 1, wherein the amounts of the thermoplastic polyester-based polyurethane are 60 to 90 parts by weight.

4. An artificial valve according to claim 1, wherein the amounts of the thermoplastic polyester-based polyurethane are 50 to 70 parts by weight.

5. An artificial blood vessel according to claim 1, wherein the amounts of the thermoplastic polyester-based polyurethane are 70 to 100 parts by weight.

6. A medical appliance according to claim 1, wherein the thermoplastic polyester-based polyurethane is composed of a straight chain polyester component derived from an aliphatic diol having at least 6 carbon atoms and an aliphatic dicarboxylic acid having at least 6 carbon atoms, said polyester having a hydroxyl number of 50 to 60, and an alkylene diisocyanate or polyoxyalkylene diisocyanate component.

* * * * *